(12) United States Patent
Soitamo et al.

(10) Patent No.: US 8,374,418 B2
(45) Date of Patent: Feb. 12, 2013

(54) METHOD AND APPARATUS RELATING TO SAMPLE CARD PUNCHING

(75) Inventors: Heimo Soitamo, Turku (FI); Ari-Pekka Kitinoja, Taivassalo (FI); Vesa Erkkila, Littoinen (FI)

(73) Assignee: Wallac Oy, Turku (FI)

( * ) Notice: Subject to any disclaimer, the term of this patent is extended or adjusted under 35 U.S.C. 154(b) by 131 days.

(21) Appl. No.: 12/937,721

(22) PCT Filed: Apr. 17, 2009

(86) PCT No.: PCT/FI2009/050286
§ 371 (c)(1),
(2), (4) Date: Mar. 3, 2011

(87) PCT Pub. No.: WO2009/130378
PCT Pub. Date: Oct. 29, 2009

(65) Prior Publication Data
US 2011/0158500 A1    Jun. 30, 2011

Related U.S. Application Data

(60) Provisional application No. 61/046,831, filed on Apr. 22, 2008.

(30) Foreign Application Priority Data

Apr. 22, 2008    (FI) ..................................... 20085343

(51) Int. Cl.
*G06K 9/00*    (2006.01)
*G01N 35/00*    (2006.01)

(52) U.S. Cl. ......................................... 382/133; 436/43

(58) Field of Classification Search .................. 382/128, 382/129, 130, 131, 132, 133, 134; 422/63, 422/65, 66, 67; 435/30, 287.3, 287.9, 309.1; 436/43, 46, 47, 48, 52, 55, 174, 177, 519, 436/528
See application file for complete search history.

(56) References Cited

U.S. PATENT DOCUMENTS

| | | | |
|---|---|---|---|
| 5,460,057 A * | 10/1995 | Ostrup ..................... | 73/864.81 |
| 5,641,682 A * | 6/1997 | Pagels et al. ................... | 436/43 |
| 2005/0053268 A1 | 3/2005 | Breen | |

FOREIGN PATENT DOCUMENTS

| | | |
|---|---|---|
| DE | 102004051508 A1 | 6/2005 |
| EP | 0437968 A | 7/1991 |
| EP | 0583078 A | 2/1994 |
| FI | 101178 B1 | 4/1998 |
| WO | WO 9720198 A | 6/1997 |
| WO | WO2009130378 | 10/2009 |

* cited by examiner

*Primary Examiner* — Abolfazl Tabataba
(74) *Attorney, Agent, or Firm* — Seppo Laine Oy; Joshua P. Wert

(57) ABSTRACT

The invention relates to method and apparatus for determining from a sample carrier containing an impregnated biological sample a sample region to be removed. The method comprises optically imaging the sample carrier into a digital matrix form, where the optical brightness of each physical location of the sample is represented by elements of the matrix; determining a first threshold value at least partly on the basis of the elements of the matrix; and calculating coordinates corresponding to the sample region to be removed from the sample carrier, the coordinates being such that the sample region contains only areas of the sample carrier having an optical brightness lower than or equal to said first threshold value. The invention allows for more efficient use of samples in sample cards.

23 Claims, 1 Drawing Sheet

METHOD AND APPARATUS RELATING TO SAMPLE CARD PUNCHING

The present invention relates to punching of sample cards containing sample sports of impregnated body fluid, in particular blood. More specifically, the invention relates to a method of recognition of the sample spots on the cards for determining the areas to be punched in order to be able to analyse the samples. The invention relates also to an apparatus carrying put said recognition and, optionally, punching.

Punching of sample cards is used in analytical sciences and industry, for example, for carrying out neonatal screening. In the method, blood samples are collected by impregnating them from sample donors to certain areas of fibrous cards so as to form sample spots on the cards. The cards are thereafter fed to an automatic card handling apparatus, which punches several small-diameter sample discs from each of the sample spots. The discs are conveyed to wells of a microtiter plate and are then subjected to (bio)chemical preparation steps and the amount of analyte(s) in the wells is determined, for example, optically. Before punching, the sample cards are digitized into pixels, meaning that they are optically imaged and transformed into a two-dimensional matrix of values, which depend on the darkness of the card at the location corresponding to pixel. Punching is carried out only from those areas, in which the pixel values are consistently lower than a pre-set threshold value (typically the cards are light-coloured, whereby blood spots show as dark areas in the image). Different thresholds may have been set for different types of sample cards.

U.S. Pat. No. 5,460,057, which is incorporated herein by reference, discloses automated instrumentation, which comprises a detection unit which observes the location of the sample on a filter paper using a method of the above kind. The purpose of the detection is to select for punching a location where the sample has absorbed through the paper.

The sample recognition method described above has considerable disadvantages. It limits the ability of the apparatus to find usable punching areas from the card in the usual case where the blood is not uniformly distributed to the card but forms a relatively arbitrary shape containing an uneven distribution of blood. Different levels of haemoglobin in the blood causes considerable variations in the darknesses of the spots. In addition, control and calibration cards used in calibrating the apparatus may have spots of varying darkness depending on their batch or sample concentration. All the above aspects result in that an unnecessarily large percentage of sample spots are disregarded and not punched at all, despite the fact that they would contain a decent sample region for the analysis. This has the undesired consequence that more blood samples need to be obtained from donors, the donors being typically newborn babies.

The aim of the invention is to provide an improved method and apparatus for recognition of sample areas for further punching. In particular, it is an aim of the invention to achieve a method and apparatus, which allow more accurate recognition of the usable sample areas and therefore have a positive effect on patient/donor comfort thanks to fewer number of or smaller samples required.

A further aim of the invention is to achieve an improved punching process.

The invention is based on the idea of determining individually for each card or even individually for each sample spot its own threshold value and calculating the punching region based on the so determined threshold value.

There is thus provided a method for determining from a sample carrier containing one or more impregnated biological samples a sample region to be removed for further sample analysis, comprising optically imaging the at least one impregnated sample in order to form an image, and based on intensity values of the image, determining the location of the sample region to be removed from said impregnated sample. This is achieved by determining a first intensity threshold value is individually for a single impregnated sample or for a plurality of impregnated samples in said sample carrier, and utilizing the first threshold value for the determination of the location of the sample region. A corresponding apparatus is provided.

According to a first aspect of the invention there is provided a method comprising optically imaging the sample carrier into a digital matrix form, where the optical brightness of each physical location of the samples is represented by elements of the matrix, determining a first threshold value at least partly on the basis of the elements of the matrix, and calculating coordinates corresponding to said sample region to be removed from said sample carrier, the coordinates being such that the sample region contains only areas of the sample carrier having an optical brightness lower than or equal to said first threshold value.

According to a second aspect of the invention the method further comprises determining a second threshold value at least partly on the basis of the elements of the matrix, and calculating said coordinates such that the region contains only areas of the sample carrier having an optical brightness higher than or equal to said second threshold value.

The punching coordinate or coordinates is/are determined such that the punched disc will entirely be contained in a continuous area having a brightness lower than the first punching threshold and, optionally, higher that the second punching threshold.

According to one aspect, pre-recorded data on dimensions of the puncher later used for performing the actual punching is used for said removal of the region is used. In this case, it is sufficient that the punching coordinates correspond to a single point in the sample card, e.g. a centre of a sample disc. This is useful if the punching tool is capable of punching discs having a predetermined size and shape, e.g. only circular discs.

According to an alternative aspect, the coordinates are sufficient to unambiguously define the punching region. That is, the punching coordinates represent a group of points in the sample card. That is, diverse shapes and/or sizes of sample discs can be produced. This is useful only if the punching tool is capable of producing discs having varying shape and/or size. In this case, the punching coordinates may comprise more than a single point, for example, the centre and the lengths of the main axes of an ellipse, or data corresponding to some other geometrical form, even the whole outline of the region to be punched.

Scanning or digital photographing may be used for carrying out the imaging.

The apparatus according to the invention comprises an optical imaging unit for imaging at least portion the sample carrier for obtaining an image, and a computing unit adapted to determine the location of said sample region by using a first threshold value determined, based on intensity values of the image, individually for a single biological sample or for a plurality of biological samples in said sample carrier. The optical imaging unit is typically adapted to image at least portion the sample carrier into a digital matrix form, where the optical brightness of each physical location of the samples is represented by elements of the matrix, and the computing unit is adapted to determine at least partly on the basis of the elements of the matrix and to calculate coordinates corresponding to said region to be removed from said sample carrier, the coordinates being such that the region contains only areas of the sample carrier having an optical brightness lower than or equal to said first threshold value.

The invention offers considerable advantages. Thus, by means of the invention it is possible to obtain sample discs with a sufficient amount of analyte more reliably and with an increased efficiency, that is, increased punched area vs. total sample area.

In particular, the present invention offers advantages in connection with punchers having a customizable cutting head and thus the capability of cutting discs of different shapes. Such punchers are capable of applying a localized cutting impact to the sample-containing sheet as opposed to one-shot punching. The localized impact is moved with respect to the sheet such that the desired fraction is detached or easily detachable from the remaining sheet. That is, the outline of the fraction is "drawn" to the sheet, for example, using a spatially controllable radiation or material stream having the ability to mechanically separate elementary parts of the sheet from each other in order to form said fraction.

Unless otherwise stated, the terms "punching" and "puncher" in this document refer to both conventional mechanical one-shot punching using, e.g. a fixed-shape cutting blade and localized-impact cutting described in this document.

By "sample carriers" we mean mainly planar substrates, which have substantial porosity so as to be able to be impregnated by a wet sample, in particular blood. In particular, the sample carrier can be a fibrous sheet, such as a paper or cardboard sheet. Sample sheets used in conventional punching are suitable to be used in connection with the present method and apparatus. Such sample sheets are typically in the form of cards, which contain a plurality of sample-receiving zones in the form of pre-printed regions in the cards.

The term "biological sample" is used to describe all kinds of biological fluids, including bodily fluids such as blood and DNA samples in particular. The term "impregnated" in this context means that the sample in question has been introduced to the receptive sample carrier in such a way that the sample has partially or entirely adhered to pores of the sample carrier. Typically, the sample is impregnated entirely into a fibrous sheet.

The terms "sample-containing portion" and "sample fraction" are used to describe the part of the sample carrier whose location on the sample carrier and, optionally, shape and size are determined by using the present invention. In detail, the above mentioned terms refer to those particular parts of the sample desired to be detached or samples that have been or are being detached from the sample carrier for being later introduced into a microplates or the like. In particular, the present invention relates to sample fractions, which can be fitted into a 96- or 384-well SBS standard microtiter plates.

The term "sample carrier holder" is used to describe any means capable of holding the sample carrier at a cutting zone in a desired position with respect to the puncher during the punching process. The sample holder can be, for example, simply a frame or plate on which the sample carrier rests or it may comprise grabber for providing a firm hold of the carrier. The sample holder may also serve so as to transport the sample carrier in and out of the cutting zone before and after cutting, respectively.

Next, the embodiments of the invention will be more closely with reference to the attached drawings.

Figure 1:
FIG. 1 depicts a photograph of a blood sample in a sample card.

FIG. 1 shows a picture of a real sample obtained from a donor in California. Dark areas represent the blood spot on a sample card and light areas represent plain substrate, which is free from blood. Due to the complex shape and intensity distribution within the blood spot, a puncher-specific threshold value would in practice result in that punching would be prevented only from the large light area on the top of the spot and that discs with too low blood amount would be punched from the lower portion of the spot. On the other hand, if the threshold value were adjusted such that the light areas at the lower part would not be punched, many other sample cards would be totally rejected. This is because the variation of intensities between different donors is by nature larger that the acceptable variation of intensity within a single blood spot. Thus, using traditional means, it is impossible to find a balance between measurement reliability and the suitability of the puncher for sample cards from donors having inherently light blood colour.

Figure 2:
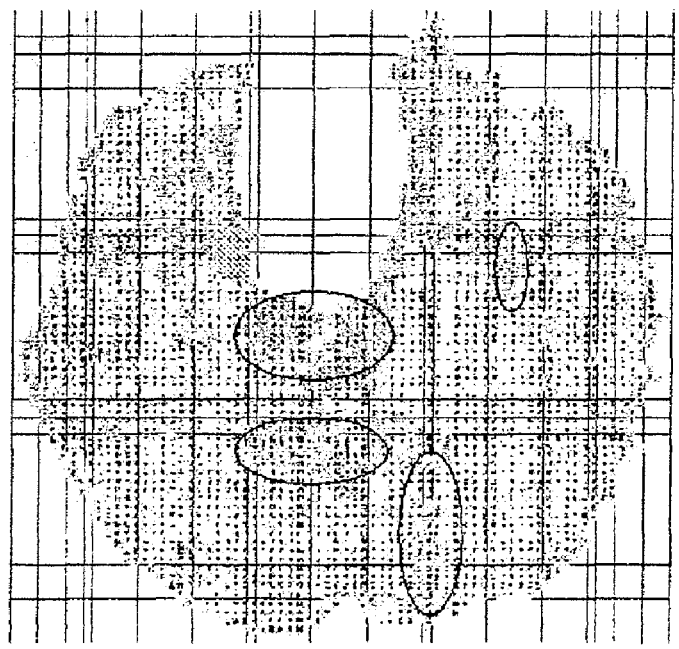
FIG. 2 shows a computer-manipulated scan of the blood sample.

FIG. 2 shows a picture of the sample of FIG. 1 in a numerical form. The ringed areas represent areas prevented from punching, defined by the present method on a spot-by-spot basis. These areas do not contain enough blood to reliably represent the donor.

According to one embodiment of the invention, areas already removed from the sample carrier and/or areas outside a predefined sample area are determined based on the values of the elements in the matrix. These elements are not used in determination of the threshold value, because they do not represent the sample under interest (but a punched hole in the sample or, for example, printed or handwritten text or other patterns in the sample card, e.g., sample donor identity information typically contained in the card).

After imaging, one can proceed by determining a continuous zone roughly (=loose tolerance) corresponding to the shape of the biological sample. Only values within said continuous zone are used for determination of the first threshold value. The continuous zone can be determined for example, by calculating a median of elements not abandoned yet, an average of the elements not abandoned yet or a histogram of the elements not abandoned yet.

If a single element of the matrix deviating considerably from other elements of the matrix, it may be determined whether the element represents noise originating from the optical imaging or a real portion of sample. In general, separate single elements deviating considerably (e.g., over 20%) from the surrounding elements may be deemed to be noise. On the other hand, element groups having such a deviating brightness may be deemed to represent real properties of the sample.

According to one embodiment, a sample carrier comprising a plurality of biological samples is used and the first threshold value is calculated individually for each of the biological samples. This allows for very different kinds of samples, even from different persons to be used on only one sample card.

Alternatively, a sample carrier comprising a plurality of biological samples is used and the first threshold value is calculated in common applying to all the biological samples. This is useful, if the samples are known to have approximately the same optical/biological properties, e.g., if all the samples in the card are from a single person.

According to one embodiment, the threshold value(s) and/or coordinate data are transmitted further to a separate sample carrier puncher adapted to perform said sample region removal and conveying steps. According to alternative embodiment, the apparatus itself contains necessary punching tools.

After determining the punching region and punching the region from the sample card in order to produce a sample-containing disc, the sample-containing disc can be subjected to biochemical analysis adapted to determine the amount of said analyte in the sample-containing disc.

According to one embodiment, the punching of the sample region is carried out using a localized cutting impact, which is moved on the sample carrier in order to detach said sample-containing disc from the sample carrier. The localized-impact cutting can be realized by exposing the absorbent sheet carrying the sample of biological matter to a high-pressure material jet, such as a liquid stream, or a radiation beam, such as a laser beam. While cutting, it is assured that the sheet remains correctly positioned during the cutting process by keeping the sheet in a suitable holder. The localized cutting impact directed to the sample results in a detached or easily detachable sample portion having a shape determined using the sample area analysis described above.

Generally speaking, the term "localized cutting impact" means any kind of relatively small-sized physical interaction capable of breaking the structure of the sample carrier at local level, such that a fraction of desired shape can be separated from the remaining sample carrier. In particular, the width of the kerf resulting from the cutting is less than 0.5 mm, in particular less than 0.3 mm. According to one embodiment, the cutting impact is based on the local increase in temperature (that is, the "burning" effect) achieved by a laser beam directed to a fibrous sample carrier. According to another embodiment, the cutting impact is based on the capability of high-speed fluid particles to break bonds in a fibrous sample carrier at a micro-level because of collisions taking place in the sample carrier. According to a further embodiment, the instantaneous area of influence of the cutting impact is point-like, that is, substantially circular in cross section. The diameter of the circle is typically less than 0.5 mm, in particular less than 0.3 mm.

According to one embodiment, the localised cutting impact is produced by using a laser source. In particular, the laser source can be a diode laser, $CO_2$-laser or a fibre laser. According to another embodiment, the localised cutting impact is achieved using a nozzle capable of spouting a high-pressure fluid jet, typically a liquid jet, in particular a water jet. The term "water" is described to include all aqueous solutions such as assay buffers.

The device may further be adapted to take the detached sample portion into a receiving recess, typically a sample well of a microtiter plate or the like, for analysis of the biological sample.

Customizable cutting as described above provides substantial advantages compared to conventional ways of cutting sample sheets. One of the main advantages of applying the present cutting method and apparatus to cutting absorbent sheets is that the form of the sample fraction to be cut can be freely chosen, even during the cutting process, for example, to match the geometry of the sample area on the sample carrier. Secondly, cutting jet and beam devices can be manufactured to be relatively small in size and thus take up less valuable space in operational areas and are less expensive to transport. Thirdly, they present functional advantages by not exposing the sheet to a conventional cutting blade, which produces less disruptive static electricity, dust and fibre particles that would otherwise compromise product quality. Avoided quality issues include impaired integrity of executed analyses due to dust and fibre particles as well as the cut samples not landing successfully into corresponding receptive wells because of static electricity accumulated on the fraction cut. Also because the sheet needs not be subjected to a typically vociferous punch-like tool, the noise level is reduced. At least laser and liquid jet "punchers" produce virtually no noise, which has an improving effect on the working environment of operators. Fourthly, the present invention is advantageous in terms of costs, since it can be manufactured using relatively inexpensive components and with its ability to produce samples of optimal shape and size, it produces little waste. Because of the disk shape optimization, also the sample donor comfort can be increased, as fewer or smaller samples need to be collected.

Imaging of the sample card can be carried on either or both sides of the card. According to one embodiment, both sides of the card are imaged and both images are used for determining the areas suitable for punching. Utilization of the image obtained from the reverse side of the card either instead or in addition to the front side image gives useful information about the degree of impregnation of the sample to the card and may thus improve the total reliability of the process.

A more detailed description of the customizable cutting method and apparatus, in particular by employing laser or water jet cutting, can be found in the still unpublished FI-application 20075863 (corresponds to U.S. 60/996,692), which is incorporated herein by reference.

The invention claimed is:

1. A method for determining from a sample carrier containing at least one impregnated biological sample a sample region to be removed for further sample analysis, comprising
optically imaging at least portion of the sample carrier into a digital matrix form, where the optical brightness of each physical location of the sample is represented by elements of the matrix,
wherein the location of the sample region is determined by
determining a first intensity threshold value at least partly on the basis of the elements of the matrix individually for said impregnated sample or for a plurality of impregnated samples in said sample carrier, and
utilizing the first threshold value for calculating coordinates corresponding to said sample region to be removed from said sample carrier, the coordinates being such that the sample region contains only areas of the sample carrier having an optical brightness lower than or equal to said first threshold value.

2. The method according to claim 1, which further comprises
determining a second threshold value at least partly on the basis of the elements of the matrix, and
calculating said coordinates such that the region contains only areas of the sample carrier having an optical brightness higher than or equal to said second threshold value.

3. The method according to claim 1, wherein in calculating said coordinates, pre-recorded data on dimensions of a tool used for said removal of the region is used.

4. The method according to claim 1, wherein said coordinates are sufficient to unambiguously define said region.

5. The method according to claim 1, further comprising
defining, based on the elements of the matrix, areas already removed from the sample carrier and/or areas outside a predefined sample area and not using matrix elements corresponding to these areas in determination of the threshold value.

6. The method according to claim 1, further comprising
determining a continuous zone roughly corresponding to the shape of the biological sample, and
using only values within said continuous zone for determination of the first threshold value.

7. The method according to claim 6, wherein a median of the elements of the matrix, an average of the elements in the matrix or a histogram of the elements of the matrix is used for determining the continuous zone.

8. The method according to claim 6, further comprising a step of determining if a single element of the matrix deviating considerably from other elements of the matrix represents noise originating from the optical imaging.

9. The method according to claim 1, further comprising transmitting the threshold value and/or coordinate data from an optical imaging and calculation unit to a sample carrier puncher adapted to perform said sample region removal and conveying steps.

10. The method according to claim 1, wherein scanning or digital photographing is used for carrying out the optical imaging.

11. The method according to claim 1, wherein a sample carrier comprising a plurality of biological samples is used and the first threshold value is calculated individually for each of the biological samples.

12. The method according to claim 1, wherein a sample carrier comprising a plurality of biological samples is used and the first threshold value is calculated in common applying to all the biological samples of the carrier.

13. A process for performing sample analysis in which the amount of predefined analyte is determined from a sample carrier containing biological samples, comprising
determining coordinates of a sample region on said sample carrier using a method comprising,
optically imaging at least portion of the sample carrier into a digital matrix form, where the optical brightness of each physical location of the sample is represented by elements of the matrix,
wherein the location of the sample region is determined by
determining a first intensity threshold value at least partly on the basis of the elements of the matrix individually for said impregnated sample or for a plurality of impregnated samples in said sample carrier, and
utilizing the first threshold value for calculating coordinates corresponding to said sample region to be removed from said sample carrier, the coordinates being such that the sample region contains only areas of the sample carrier having an optical brightness lower than or equal to said first threshold value,
punching said sample region from the sample card in order to form a sample-containing disc, and
subjecting the sample disc to biochemical analysis adapted to determine the amount of said analyte in the sample-containing disc.

14. The process according to claim 13, wherein said step of punching the sample region is carried out using a localized cutting impact, such as a laser beam or a liquid jet, which is moved on the sample carrier in order to detach said sample-containing disc from the sample carrier.

15. An apparatus for determining from a sample carrier containing at least one impregnated biological sample a sample region to be removed and conveyed for sample analysis, comprising
an optical imaging unit for imaging at least portion the sample carrier into a digital matrix form where the optical brightness of each physical location of the samples is represented by elements of the matrix, and
a computing unit adapted to
determine, based on the matrix values, a first threshold value individually for a single biological sample or for a plurality of biological samples in said sample carrier,
calculate coordinates corresponding to said region to be removed from said sample carrier, the coordinates being such that the region contains only areas of the sample carrier having an optical brightness lower than or equal to said first threshold value.

16. The apparatus according to claim 15, wherein the computing unit is further adapted to
determine a second threshold value at least partly on the basis of the elements of the matrix, and
calculate said coordinates such that the region contains only areas of the sample carrier having an optical brightness higher than or equal to said second threshold value.

17. The apparatus according to claim 15, which contains a memory unit containing data on dimensions of a tool to be used for said removal of the region and wherein the computing unit is adapted to calculate said coordinates using said data.

18. The apparatus according to claim 15, wherein the computing unit is adapted to calculate coordinates sufficient to unambiguously define said region.

19. The apparatus according to claim 15, wherein the computing unit is adapted to define, based on the elements of the matrix, areas already removed from the sample carrier and/or areas outside a predefined sample area and not using matrix elements corresponding to these areas in determination of the threshold value.

20. The apparatus according to claim 15, wherein the computing unit is adapted to determine from the sample carrier a continuous zone roughly corresponding to the shape of the biological sample, and, using only values within said continuous zone, determine the first threshold value.

21. The apparatus according to claim 15, further comprising a communications unit for transmitting the threshold value and/or coordinate data to a sample carrier puncher adapted to perform said sample region removal and conveying steps using said data.

22. The apparatus according to claim 15, wherein the optical imaging unit comprises a scanner or a digital camera.

23. The apparatus according to claim 15, which further comprises a punching tool for removing said sample region from the sample carrier.

* * * * *